United States Patent
Bates et al.

(10) Patent No.: US 8,105,336 B2
(45) Date of Patent: *Jan. 31, 2012

(54) ATRAUMATIC MEDICAL RETRIEVAL DEVICE

(75) Inventors: James S. Bates, Sparta, NJ (US); Like Que, Bloomington, IN (US); James W. Riley, Bloomington, IN (US); James A. Teague, Spencer, IN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/706,074

(22) Filed: Feb. 16, 2010

(65) Prior Publication Data

US 2010/0268246 A1 Oct. 21, 2010

Related U.S. Application Data

(63) Continuation of application No. 10/949,874, filed on Sep. 27, 2004, now Pat. No. 7,691,111, which is a continuation of application No. 10/360,417, filed on Feb. 7, 2003, now Pat. No. 7,077,849, which is a continuation of application No. 09/756,093, filed on Jan. 8, 2001, now Pat. No. 6,527,781, which is a continuation of application No. 09/296,327, filed on Apr. 22, 1999, now Pat. No. 6,224,612.

(60) Provisional application No. 60/082,810, filed on Apr. 23, 1998, provisional application No. 60/105,448, filed on Oct. 23, 1998.

(51) Int. Cl.
*A61B 17/22* (2006.01)
*B23P 19/04* (2006.01)

(52) U.S. Cl. .......................................... 606/127; 29/428

(58) Field of Classification Search .................. 606/127, 606/114, 115, 113, 116, 110, 128, 200; 29/428
See application file for complete search history.

(56) References Cited

U.S. PATENT DOCUMENTS

| | | | |
|---|---|---|---|
| 651,395 A | 6/1900 | Strapp |
| 1,054,960 A | 3/1913 | Butner |
| 2,556,783 A | 6/1951 | Wallace |
| 2,767,703 A | 10/1956 | Nieburgs |
| 3,765,296 A | 10/1973 | Fischer |
| 3,791,387 A | 2/1974 | Itoh |
| 3,828,790 A | 8/1974 | Curtiss et al. |
| 3,955,578 A | 5/1976 | Chamness et al. |
| 4,198,960 A | 4/1980 | Utsugi |
| 4,326,530 A | 4/1982 | Fleury, Jr. |

(Continued)

FOREIGN PATENT DOCUMENTS

DE 2804058 8/1978

(Continued)

OTHER PUBLICATIONS

Patent Cooperation Treaty, *International Search Report*, Dec. 3, 1999 for application having Serial No. PCT/US99/08490.

(Continued)

*Primary Examiner* — Pedro Philogene
(74) *Attorney, Agent, or Firm* — Finnegan, Henderson, Farabow, Garrett & Dunner, L.L.P.

(57) ABSTRACT

Baskets with atraumatic distal tips allow the capture of material from difficult-to-reach areas of the body, while reducing the risk of tissue damage.

19 Claims, 16 Drawing Sheets

U.S. PATENT DOCUMENTS

| | | | |
|---|---|---|---|
| 4,347,846 A * | 9/1982 | Dormia | 606/127 |
| 4,427,014 A | 1/1984 | Bel et al. | |
| 4,590,938 A * | 5/1986 | Segura et al. | 606/127 |
| 4,655,219 A | 4/1987 | Petruzzi | |
| 4,691,705 A | 9/1987 | Okada | |
| 4,718,419 A | 1/1988 | Okada | |
| 4,790,812 A | 12/1988 | Hawkins et al. | |
| 4,807,626 A * | 2/1989 | McGirr | 606/127 |
| 4,893,621 A | 1/1990 | Heyman | |
| 4,994,079 A | 2/1991 | Genese et al. | |
| 5,010,894 A | 4/1991 | Edhag | |
| 5,011,488 A | 4/1991 | Ginsburg | |
| 5,057,114 A | 10/1991 | Wittich et al. | |
| 5,064,428 A | 11/1991 | Cope et al. | |
| 5,084,054 A | 1/1992 | Bencini et al. | |
| 5,098,440 A | 3/1992 | Hillstead | |
| 5,108,418 A | 4/1992 | Lefebvre | |
| 5,147,378 A | 9/1992 | Markham | |
| 5,163,942 A | 11/1992 | Rydell | |
| 5,171,233 A | 12/1992 | Amplatz et al. | |
| 5,171,314 A | 12/1992 | Dulebohn | |
| 5,207,686 A | 5/1993 | Dolgin | |
| 5,290,294 A | 3/1994 | Cox et al. | |
| 5,365,926 A | 11/1994 | Desai | |
| 5,376,100 A | 12/1994 | Lefebvre | |
| 5,403,324 A | 4/1995 | Ciervo et al. | |
| 5,417,684 A | 5/1995 | Jackson et al. | |
| 5,421,832 A | 6/1995 | Lefebvre | |
| 5,454,370 A | 10/1995 | Avitall | |
| 5,462,553 A | 10/1995 | Dolgin | |
| 5,486,183 A | 1/1996 | Middleman et al. | |
| 5,496,330 A | 3/1996 | Bates et al. | |
| 5,499,981 A | 3/1996 | Kordis | |
| 5,549,661 A | 8/1996 | Kordis et al. | |
| 5,613,973 A | 3/1997 | Jackson et al. | |
| 5,632,746 A | 5/1997 | Middleman et al. | |
| 5,647,870 A | 7/1997 | Kordis et al. | |
| 5,658,296 A | 8/1997 | Bates et al. | |
| 5,693,069 A | 12/1997 | Shallman | |
| 5,725,525 A | 3/1998 | Kordis | |
| 5,810,876 A | 9/1998 | Kelleher | |
| 5,823,189 A | 10/1998 | Kordis | |
| 5,846,238 A | 12/1998 | Jackson et al. | |
| 5,853,411 A | 12/1998 | Whayne et al. | |
| 5,928,228 A * | 7/1999 | Kordis et al. | 606/41 |
| 5,989,266 A | 11/1999 | Foster | |
| 5,991,650 A | 11/1999 | Swanson et al. | |
| 6,013,086 A | 1/2000 | Ouchi et al. | |
| 6,168,603 B1 | 1/2001 | Leslie et al. | |
| 6,174,318 B1 * | 1/2001 | Bates et al. | 606/127 |
| 6,224,612 B1 | 5/2001 | Bates et al. | |
| 6,368,328 B1 | 4/2002 | Chu et al. | |
| 6,500,182 B2 | 12/2002 | Foster | |
| 6,527,781 B2 | 3/2003 | Bates et al. | |
| 7,691,111 B2 * | 4/2010 | Bates et al. | 606/114 |

FOREIGN PATENT DOCUMENTS

| | | |
|---|---|---|
| DE | 3522649 A1 | 1/1986 |
| DE | 8501297 | 2/1986 |
| DE | 3501707 | 7/1986 |
| DE | 8707515 | 7/1987 |
| DE | 8707516 | 8/1987 |
| EP | 0 123 175 | 10/1984 |
| EP | 0 160 870 B1 | 7/1991 |
| EP | 0 512 729 | 11/1992 |
| EP | 0 512 729 | 7/1995 |
| EP | 0 737 450 | 10/1996 |
| JP | 52-030574 | 3/1977 |
| JP | 60-241430 | 11/1985 |
| JP | 63-111851 | 5/1988 |
| JP | 01-95910 | 6/1989 |
| JP | 1-172813 | 12/1989 |
| JP | 6-154231 | 6/1994 |
| JP | 8-511438 | 12/1996 |
| SU | 1228837 | 5/1986 |
| WO | WO 92/05828 | 4/1992 |
| WO | WO 94/21166 | 9/1994 |
| WO | WO 95/05129 | 2/1995 |
| WO | WO 96/15728 | 5/1995 |
| WO | WO 98/36694 | 8/1998 |

OTHER PUBLICATIONS

English language version of a Nov. 28, 2003 action issued by the Japanese Patent Office.
U.S. Appl. No. 60/039,448, filed Feb. 24, 1997.
Office Action from the Japanese Patent Office dated Sep. 7, 2004.
English translation of Decision of Appeal from the Japanese Patent Office dated Dec. 12, 2006 in Japanese Patent Application 11-553187 (8 pages).

* cited by examiner

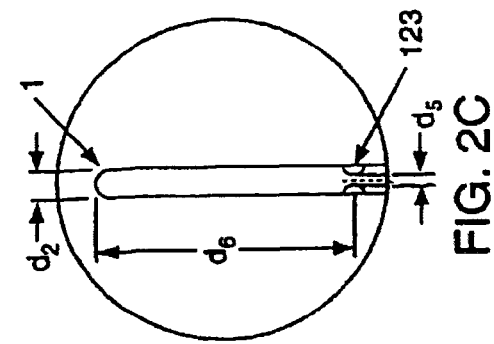
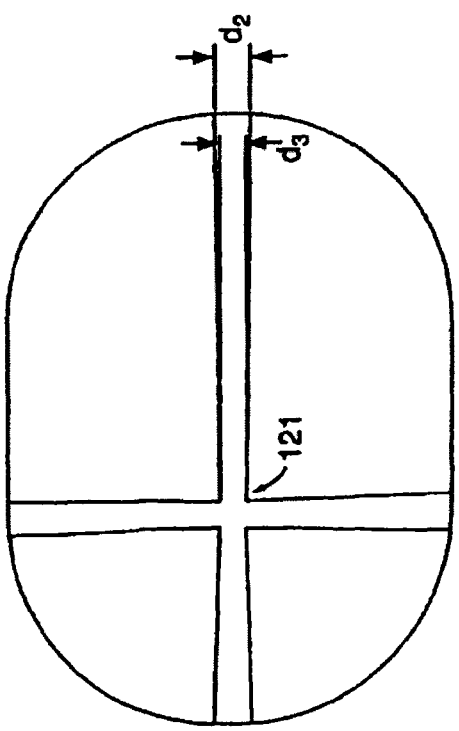
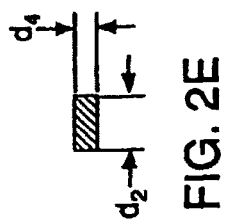
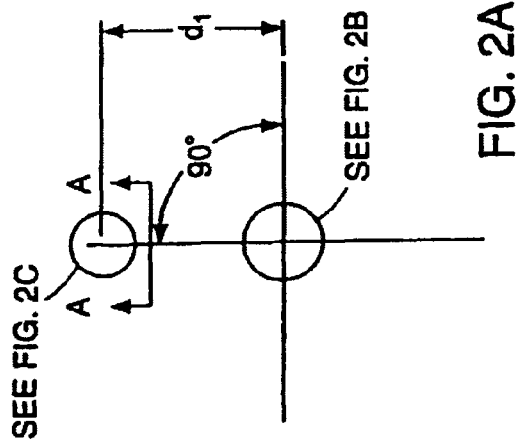

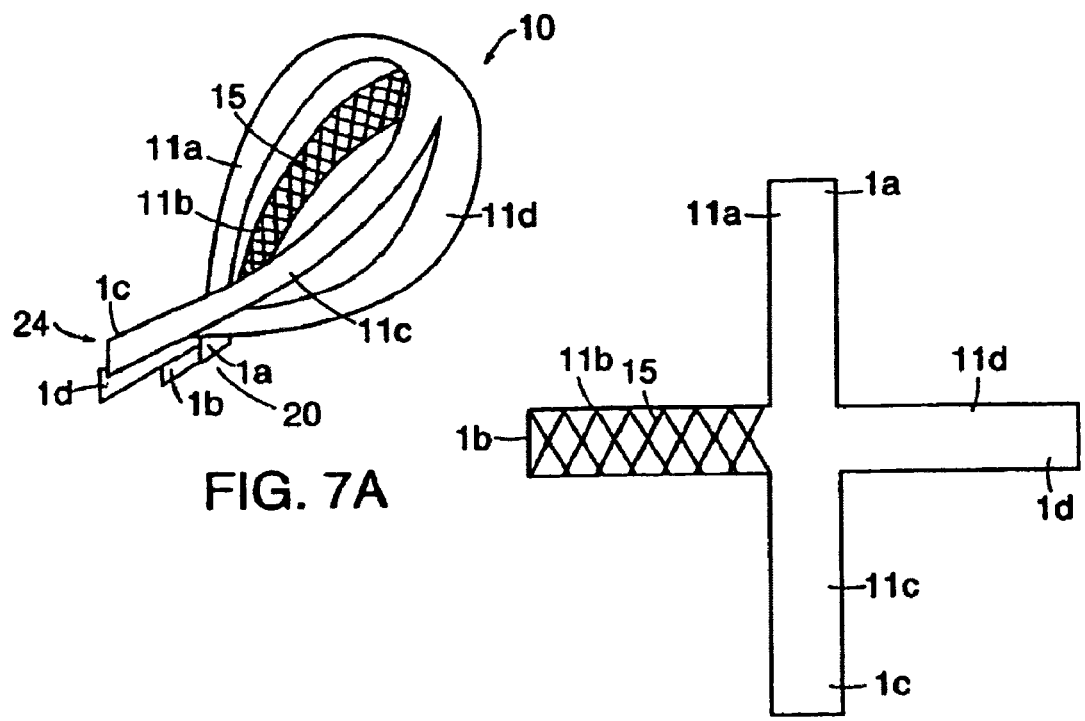
FIG. 7A
FIG. 7B
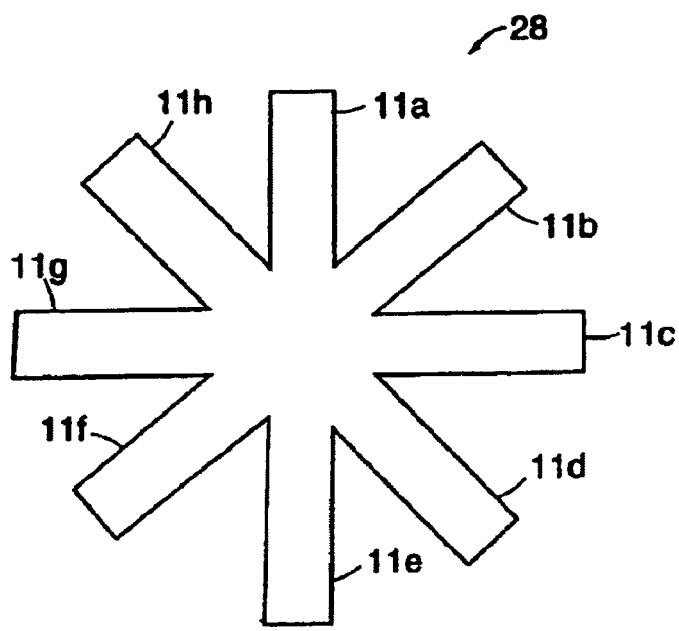
FIG. 8

ATRAUMATIC MEDICAL RETRIEVAL DEVICE

CROSS-REFERENCE TO RELATED APPLICATIONS

This application is a continuation of U.S. application Ser. No. 10/949,874, filed Sep. 27, 2004 now U.S. Pat. No. 7,691, 111, which is a continuation of U.S. patent application Ser. No. 10/360,417, filed Feb. 7, 2003 (now U.S. Pat. No. 7,077, 849), which is a continuation of U.S. patent application Ser. No. 09/756,093, filed Jan. 8, 2001 (now U.S. Pat. No. 6,527, 781), which is a continuation of U.S. patent application Ser. No. 09/296,327, filed Apr. 22, 1999 (now U.S. Pat. No. 6,224, 612), which claims priority to provisional U.S. Application No. 60/082,810, filed Apr. 23, 1998, and provisional U.S. Application No. 60/105,448, filed Oct. 23, 1998. The complete disclosures of all of these patent application are incorporated by reference herein.

TECHNICAL FIELD

The invention relates generally to medical devices for retrieving material from within a body. More particularly, the invention relates to medical retrieval baskets that have atraumatic distal ends that are contoured or tipless both to minimize the chances of damage to tissue during use and to enhance the ability of the basket to capture material (e.g., stones) disposed or lodged in "pockets" or other areas that are difficult to access in the body.

BACKGROUND INFORMATION

Known stone retrieval devices typically have baskets that are constructed by joining multiple legs together at a base of the basket and at a distal end or tip of the basket such that a "cage" is formed. At the distal tip, the individual legs are joined by soldering, adhesives, etc. such that a protruding tip results. This protrusion or outward projection at the distal end of the basket can poke tissue and cause tissue trauma. In general, the tips or ends of known baskets protrude outward and thus can cause damage by poking or piercing tissue. Also, the protruding tips of known baskets generally do not permit access to or intimate contact with certain areas within the body such as "pockets," and thus stones residing in such areas are difficult or impossible to retrieve with known baskets.

SUMMARY OF THE INVENTION

It is an object of the invention to provide a medical retrieval basket that does not have a substantially protruding distal basket end or basket tip. That is, a basket according to the invention is atraumatic and does not have any significant distal protrusion or outward projection that can poke tissue, pierce tissue, or otherwise cause trauma to tissue.

It is another object of the invention to provide a medical retrieval basket that permits access to and/or intimate contact with certain areas within the body such as "pockets" where material to be retrieved (e.g., stones) might reside or be lodged, impacted, or embedded. A tipless or contoured tip basket arrangement can access these areas and retrieve material from those areas whereas a conventional basket with a traumatic tip would not be able to do so because of the traumatic protruding tip that prevents intimate contact between the distal end of the basket and body tissue.

It is yet another object of the invention to provide a method of using such baskets to retrieve material from within a body.

The material can be biological or foreign matter. The material can be, for example, urological stones or any of a variety of other types of material found in the body.

A basket according to one aspect of the invention is tipless and thus lacks a protruding end or tip. At least a distal end portion of the basket can be formed from a single piece of material to achieve the desired tipless feature. The one-piece construction of at least the distal end portion of the tipless basket can be achieved by removing the desired profile from a flat sheet of construction material or by using an injection mold process. With this type of single unit, one-piece construction, the basket legs require joining only at the base of the basket where the basket is attached to a cable, coil, wire, etc., that connects the basket to a proximal handle mechanism. This single unit feature of baskets according to the invention can be achieved in a variety of ways including stamping, photoetching, laser cutting, and injection molding. Also, various materials can be used to form the tipless one-piece unit or the entire basket such as metal, polymers, ceramics, powdered metals, thermal plastic composites, etc. Combinations of these or other materials also may be used to manufacture a basket according to the invention.

The invention generally relates to a medical retrieval device that comprises a sheath, a handle, and an atraumatic basket. The sheath has a proximal end and a distal end. The handle is located at the proximal end of the sheath. The basket can remove material from a body, and it has a collapsed position where the basket is enclosed within the sheath and an expanded position where the basket extends from the distal end of the sheath. The basket can have three or more legs (e.g., four, five, or six legs). At least a distal end portion of the basket is substantially tipless and defined by a shape or profile which comprises a single continuous unit. In another embodiment of the invention, the atraumatic basket is formed by a plurality of wires, each wire forming a loop with a small protrusion at the very distal end of the basket.

In accordance with one aspect of the invention, the atraumatic basket has a distal end portion defined by a single continuous, one-piece unit. The atraumatic basket can include the following features. The distal end portion of the atraumatic basket can be non-perforated or perforated to, for example, allow a guidewire or lithotripsy device (laser) to extend through the sheath and through the end of the basket. The shape of the distal end portion of the atraumatic basket can be formed from, for example, metal, metal alloys, a ceramic material, a powdered metal, or a polymer. The basket legs, each of which has an inner surface and an outer surface, can have at least a portion of their inner surfaces coated with an anti-slip material, textured, or roughened in some manner to enhance the ability of the basket to grip and hold material. The atraumatic basket can be made by one-piece construction forming, as a single continuous one-piece unit, a shape having three or more legs, for example, a y-shape, x-shape, t-shape or star-shape, and then bending the legs of the shape to form at least a distal portion of a three-dimensional basket structure that is useful for retrieving objects. Other shapes such as a double loop may be used to form the distal portion of the basket. Shapes other than the ones described here also may be used to form the distal portion of the basket The shape can be stamped, etched, and/or cut from a continuous sheet of material. Alternatively, the shape could be achieved by injection molding.

In another embodiment of an atraumatic wire basket, the distal ends of the basket wires insert into an inverted cap at the distal basket tip.

Another aspect of the invention relates to a method for manufacturing a basket for a medical retrieval device comprising the steps of forming, as a single continuous unit, a shape having three or more legs and bending the legs of the shape to form at least a portion of a three-dimensional basket structure for retrieving objects. The shape can be stamped, etched or cut from a continuous sheet of material. The shape can also be injection molded.

Yet another aspect of the invention features a method for retrieving material from a body including the steps of inserting an extractor into a body, the extractor including a basket having three or more legs and wherein at least a distal end portion of the basket is defined by a shape which comprises a single continuous unit, capturing the material within the basket and withdrawing the extractor from the body to remove the material from the body.

The foregoing and other objects, aspects, features, and advantages of the invention will become more apparent from the following description and from the claims.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

FIG. 2A illustrates a top view of one embodiment of an X-profile, one-piece construction of a distal end portion of the basket of the invention.

FIG. 2B illustrates details of the center of the X-profile illustrated in FIG. 2A.

FIG. 2C illustrates details of the end of one leg of the X-profile illustrated in FIG. 2A.

FIG. 2D illustrates embodiments of a cross-section of one of the legs illustrated in FIG. 2A.

FIG. 2E illustrates another embodiment of a cross-section of one of the legs illustrated in FIG. 2A.

FIG. 7A is an embodiment according to the invention of a three-dimensional tipless basket structure formed from a single continuous piece of material, for example, the stamped shape illustrated in FIG. 6A.

FIG. 7B is the distal end profile illustrated in FIG. 6A including a textured inner surface of one leg.

FIG. 8 is a top view of an embodiment according to the invention of another stamped shape that can be formed into a basket or a portion of a basket by bending the legs of the shape, according to the invention.

DESCRIPTION

Figure 1B:
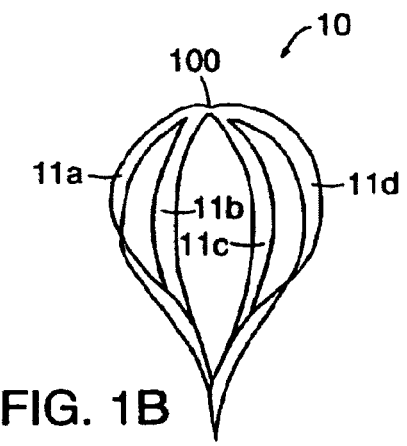
FIG. 1B illustrates a side view of an embodiment according to the invention of a three-dimensional atraumatic tipless basket formed by bending and shaping the legs of the X-profile illustrated in FIG. 1A.

All of the following embodiments of the invention generally have at least one thing in common, a basket of a medical retrieval device having a substantially atraumatic tip according to the invention. The basket 10, shown by way of example in FIG. 1F, is the type that can be collapsed within a sheath 12 for entry into the body. A medical device or extractor that includes the basket 10 of the invention also includes the sheath 12 and a proximal handle 8. The handle 8, sheath 12, and basket 10 illustrated in FIGS. 1E and 1F are not shown in their correct size or proportion to each other. The size of the entire sheath is dimensioned to fit the requirements of its application in the body. For example, for urological applications, the size of the device is typically 1.7-8.0 Fr. The sheath 12 has at least one lumen 14 therein, may be made from a single material, and extends from the handle 8 to a distal sheath end 16. An elongated member such as a cable, coil, shaft, guidewire or mandril wire 18 extends within the lumen 14 from an actuating mechanism 4 at the device handle 8 to the base 20 of the basket 10, where the cable 18 is attached to the basket base 20. Operation of the actuating mechanism 4 by an operator causes the basket 10 to move in and out of the sheath 12 between a collapsed position within the sheath 12 as illustrated in FIG. 1F to an extended position outside of the sheath 12 where the basket 10 is open/expanded and extending beyond the distal end of the sheath 16 as shown in FIG. 1E. Alternatively, the mechanism 4 can cause movement of the sheath 12 to advance the sheath 12 over the stationary basket 10 and cable 18 combination, to thereby collapse the basket 10 within the sheath 12, and the mechanism 4 can slide the moveable sheath 12 back to expose the stationary basket 10 and allow it to open/expand. In general, both types of basket/sheath movement configurations and related handle mechanisms are known, and can be seen in existing product designs available from, for example, Boston Scientific Corporation (Natick, Mass.). With the basket collapsed within the sheath 12 as shown in FIG. 1F, the sheath 12 can be inserted into the body by an operator to a site in the body where the material to be retrieved is located (e.g., a stone in the ureter). By putting the basket 10 into its open/expanded position, as illustrated in FIG. 1E, the basket 10 dilates the body tract in which it has been placed and can be manipulated by the operator to entrap or capture material within the basket 10. The basket 10 and/or the sheath 12 can then be moved to cause the legs 11a, 11b, 11c, 11d of the basket 10 to close around the material and capture it. The captured material is then withdrawn from the body along with the sheath and the basket that is holding the material.

Figure 1C:
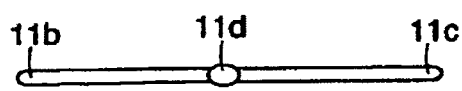
FIG. 1C illustrates a side view of an embodiment according to the invention of the X-profile illustrated in FIG. 1A.
Figure 1D:
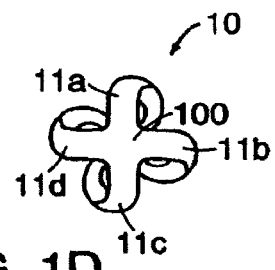
FIG. 1D illustrates an embodiment according to the invention of an end view of the X-profile illustrated in FIG. 1A.
Figure 1A:
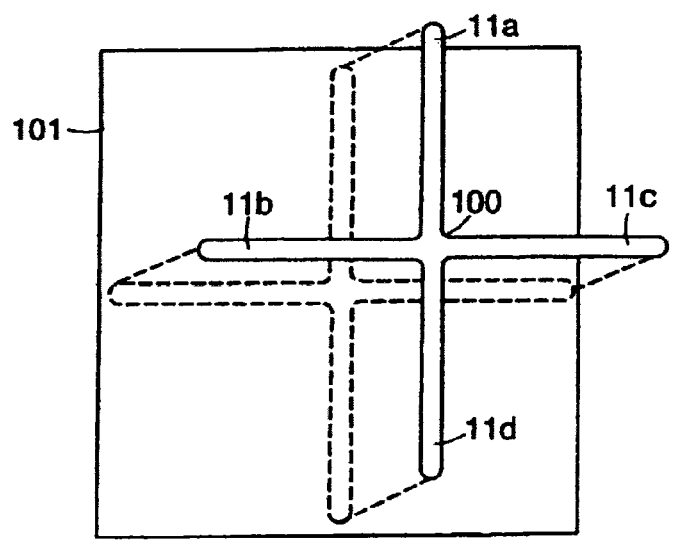
FIG. 1A illustrates a top view of an X-profile embodiment of a one-piece construction of at least a distal end portion of a medical retrieval basket removed from a single piece of substantially flat material according to the invention.
Figure 1E:
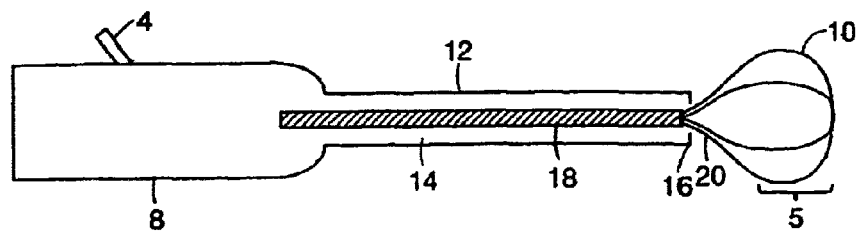
FIG. 1E illustrates one embodiment of a medical retrieval device with an atraumatic basket according to the invention with the basket in an expanded position.
Figure 1F:
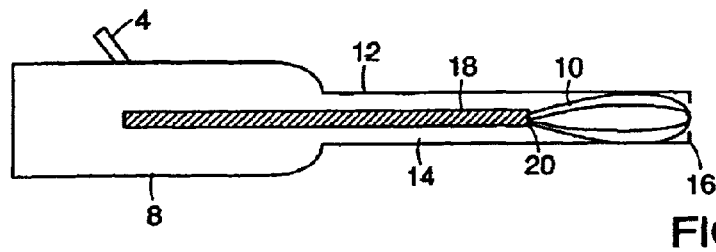
FIG. 1F illustrates one embodiment of a medical retrieval device with an atraumatic basket according to the invention with the basket in a collapsed position.

In one aspect, according to the invention, a basket 10 of a device for retrieving biological or foreign material from a body has a plurality of legs, for example, as shown in FIG. 1B, four legs 11a, 11b, 11c, 11d. An end-on view of the basket 10 in FIG. 1D illustrates a substantially tipless or atraumatic distal end 100. A small, insubstantial protrusion or depression may remain at the distal tip as a result of the manufacturing process. Such features on the basket tip do not poke, tear, pierce, perforate, bruise or otherwise inflict injury or cause trauma to the tissue and may enhance basket performance. In one embodiment, for example, the legs 11a, 11b, 11c, 11d and the atraumatic basket 10 can be cut, etched, stamped or otherwise removed as a single shape or profile from a substantially flat piece of material 101 as illustrated in FIG. 1A. In another embodiment, referring to FIGS. 1E, 1G and 6B, just the distal end portion 5 of the basket 10 is removed as a single shape or profile from a single piece of substantially flat material. Alternatively, the basket 10 or distal end portion 5 can be injection molded into the desired shape by, for example, plastic injection molding, metal-injection-molding (MIM) or by compression of metal powders. As illustrated in FIG. 1A and FIG. 1C, the starting profile for the basket 10 or the basket end portion 5 can be an X-profile or X-shape. After removal of the X-profile from the flat material, the three-dimensional basket 10 or distal end portion 5 of the basket 10 can be formed by bending and shaping the legs of an X-profile. The starting profile may be asymmetrical. For example, in other embodiments, the starting profile of the basket 10 or the distal end portion 5 can be y-shaped, t-shaped or star-shaped.

Figure 1G:
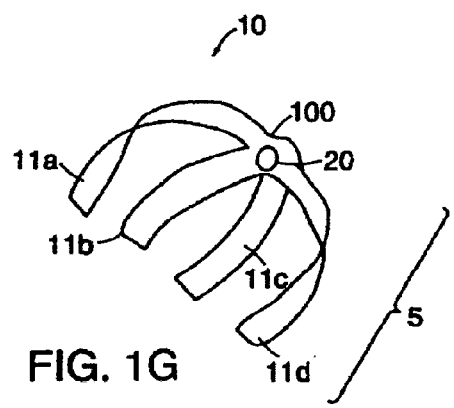
FIG. 1G illustrates a side view of one embodiment of the invention of a distal end portion of a basket formed by bending and shaping the legs of the X-profile illustrated in FIG. 1A.
Figure 1H:
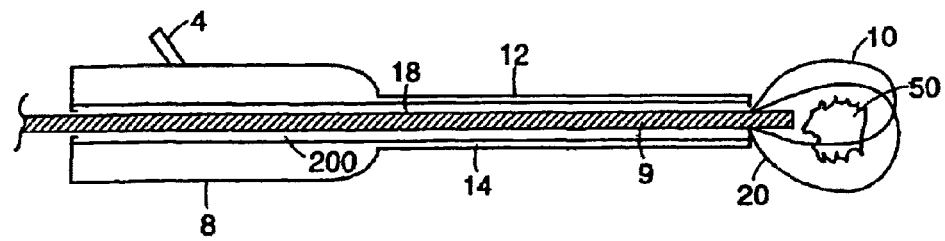
FIG. 1H illustrates an embodiment of the medical retrieval device according to the invention with a lithotriptic device extending into the basket lumen.

With continued reference to FIGS. 1B and 1D, the distal end 100 of the basket 10 is uniform, contoured, and substantially without any protruding surface features. That is, in accordance with the invention, the distal end 100 of the basket 10 is substantially devoid of knobs, protrusions, fasteners, or outward projections. The distal end 100 of the basket 10 may be perforated 20 as illustrated in FIG. 1G to permit a guidewire (not shown) to extend through the sheath 12 and out the end of the basket 10 through the perforation 20. Referring to FIG. 1H, alternatively, a ram-rod, laser or other lithotriptic device 9 is longitudinally disposed in a channel 200 of sheath 12. Channel 200 extends through the proximal end 20 of the basket 10. In operation, a stone 50 is captured in the lumen of the basket 10. The lithotriptic device is advanced beyond the proximal basket end into the basket until the lithotriptic device approaches the stone 50. The stone 50 is then fragmented by lithotripsy. The fragmented stones are removed from the body while entrapped within the basket 10.

No adhesive or any other attachment material or device is used at the distal end 100 of the basket 10 to hold the legs together as at least the distal ends of the legs are formed by a profile including distal leg portions extracted from a single piece of sheet-like material as illustrated in FIGS. 1A and 1C to form a tipless atraumatic three-dimensional basket as illustrated in FIG. 1B. The distal end 100 of the basket 10 is substantially atraumatic in that it has no substantial outward projections or protrusions that might cause injury or trauma to tissue and/or that might present an impediment to contacting the distal end 100 of the basket 10 directly and intimately with tissue.

Figure 2F:
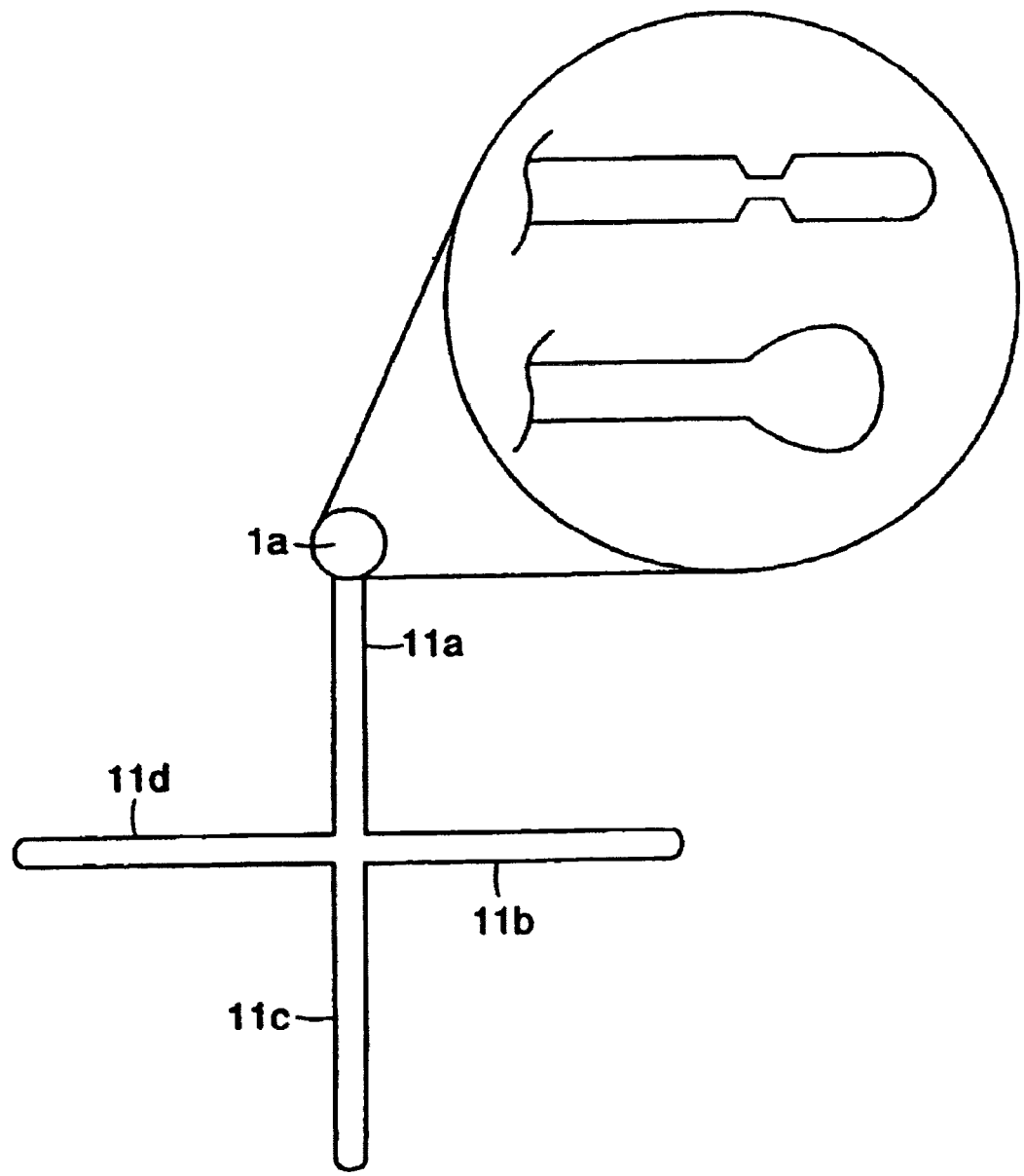
FIG. 2F illustrates one embodiment of a modification of the end of a basket leg.

In one embodiment, referring to FIGS. 2A-2E, a medical device of the invention includes a plurality of legs forming the basket 10. The legs can have various cross-sectional shapes, for example, as shown in FIGS. 2D and 2E. Other cross-sectional shapes for the legs of the basket 10 include, but are not limited to, a D-shape, a V-shape, a B-shape, rectangular, and cylindrical (not shown). Typically, the length of the legs 11a, 11b, 11c, 11d is about 0.5 to 3.5 inches, for example, 1.1 to 1.5 inches, the width of the leg is about 0.005 inches to 0.015 inches and the thickness of the legs is 0.028 inches to 0.045 inches. The ends 1 of the basket legs 11 may be modified by narrowing, enlarging or grooving the end for example, as shown in FIG. 2F, to ease assembly and/or strengthen the basket when the ends of the basket legs are brought together.

Referring to FIGS. 2A-2C and 2E, a typical basket end portion may have the following features. The basket end portion can have four legs, the legs being approximately 90° apart. The leg length $d_1$ is 1.1 inches to 1.25 inches, leg width $d_2$ is 0.010 inches to 0.012 inches, leg width $d_3$ is 0.006 inches to 0.008 inches, and leg thickness $d_4$ is 0.005±0.0003 to 0.0032±0.003 inches. At the intersection 121 of the four legs, the four corners have a slight radius as shown in FIG. 2B. The ends 1 of the legs as illustrated in FIG. 2C have a full radius. Notches or cut-outs 123 are located 0.100 inches ($d_6$) from the end 1 of the leg and have a radius of 0.003-0.004 inches with a minimum distance ($d_5$) of 0.004 inches between the apex of the notches. The "X" profile illustrated in FIG. 2A may be removed from a flat annealed, superelastic, nickel-titanium sheet having a pickled surface and active $A_f$ of 15±5° C.

The basket 10 or distal end 100 of the basket 10 can be formed from various materials such as stainless steel, metal alloys, superelastic materials, shape memory materials, powdered metals, ceramics, thermal plastic composites, ceramic composites, polymers, etc. Also, combinations of these and other materials can be used.

Figure 3A:
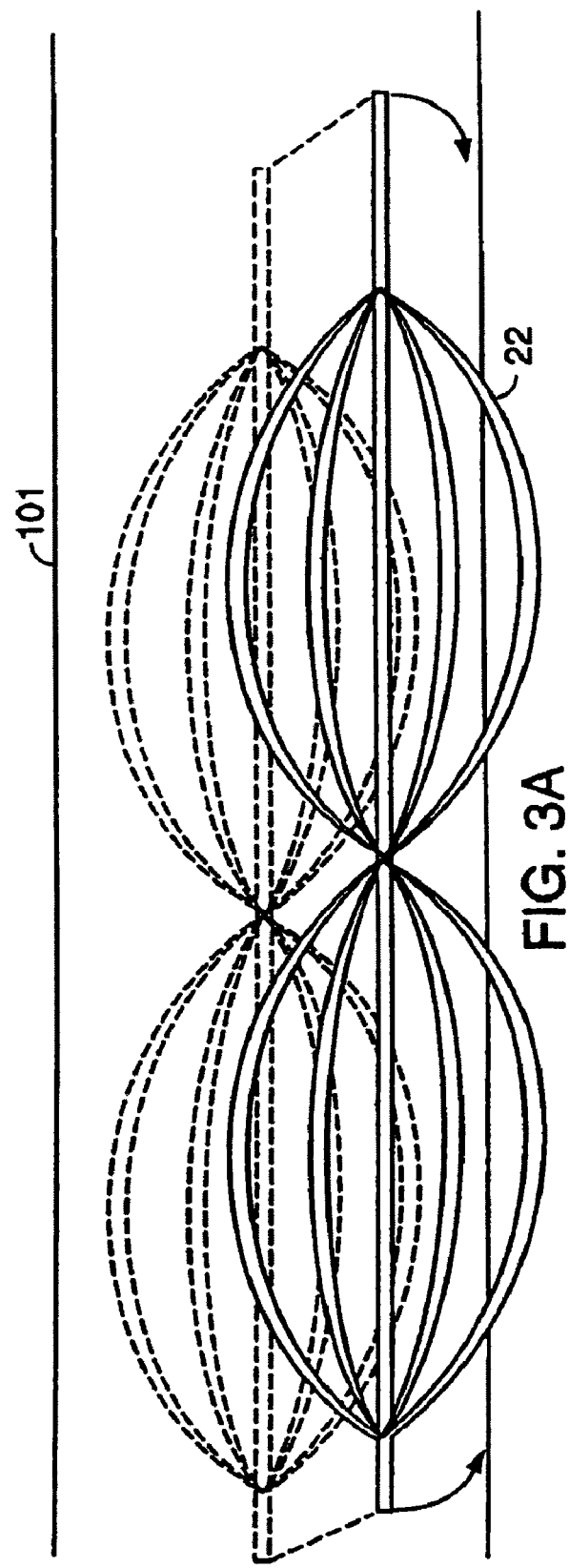
FIG. 3A illustrates a top view of a parachute-shaped profile embodiment of a one-piece construction of a medical retrieval basket removed from a single piece of substantially flat material according to the invention.
Figure 3C:
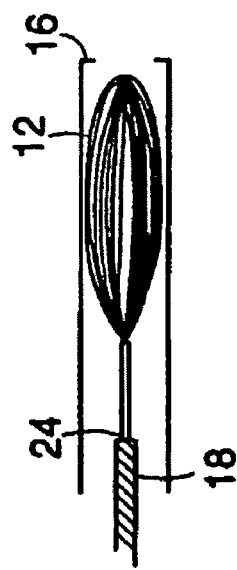
FIG. 3C illustrates the basket of FIG. 3B enclosed within a sheath.
Figure 3D:
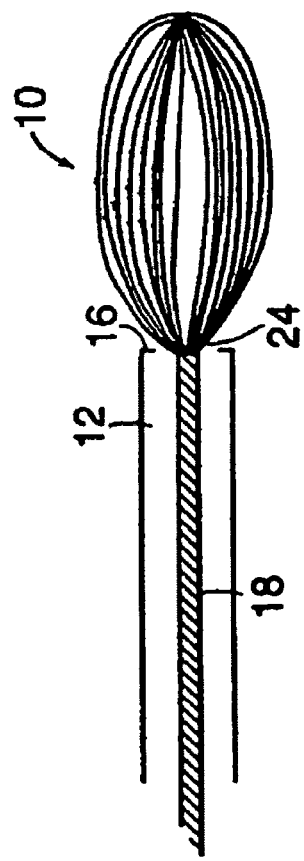
FIG. 3D illustrates the basket of FIG. 3B extended from the distal end of the sheath.
Figure 3B:
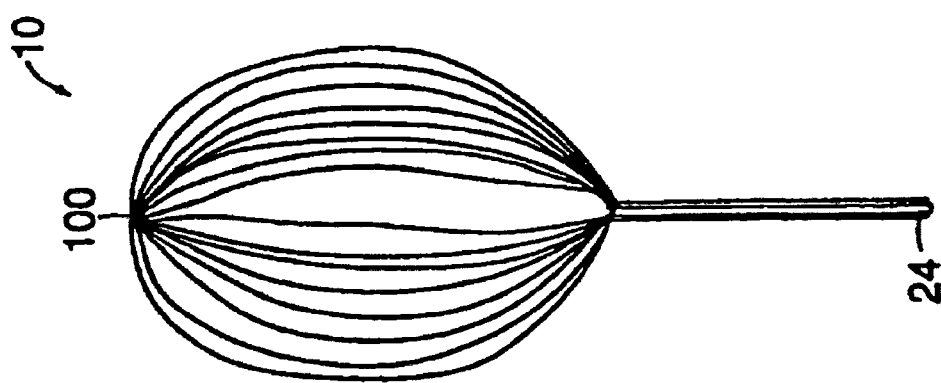
FIG. 3B illustrates a side view of an embodiment according to the invention of a three-dimensional atraumatic tipless basket formed by bending and shaping the profile of the parachute shape illustrated in FIG. 3A.

The atraumatic basket 10 can assume shapes more complex than one with three or more legs running parallel and longitudinally from the distal end of the basket to the basket base. For example, referring to FIG. 3A, a single-unit hourglass profile 22 can be removed from a single piece of sheet-like material 101 by stamping, etching, or cutting, for example, according to the invention. A three-dimensional basket 10 can be created by folding the single-unit hourglass profile, as illustrated by the arrows in FIG. 3A, into a substantially parachute-shaped configuration as shown in FIG. 3B. Heat treatment, cold-forming, or other shaping processes using a ball-shaped die is then performed on the parachute-shaped configuration to shape the profile into a three-dimensional basket 10. The distal end 100 of this basket 10 is tipless and atraumatic. The proximal end 24 of basket 10 can be joined to a cable 18 within a sheath 12 as illustrated in FIG. 3C. The basket 10 is moveable relative to the sheath 12 from a collapsed basket position, shown in FIG. 3C to an open basket position shown in FIG. 3D.

Figure 4A:
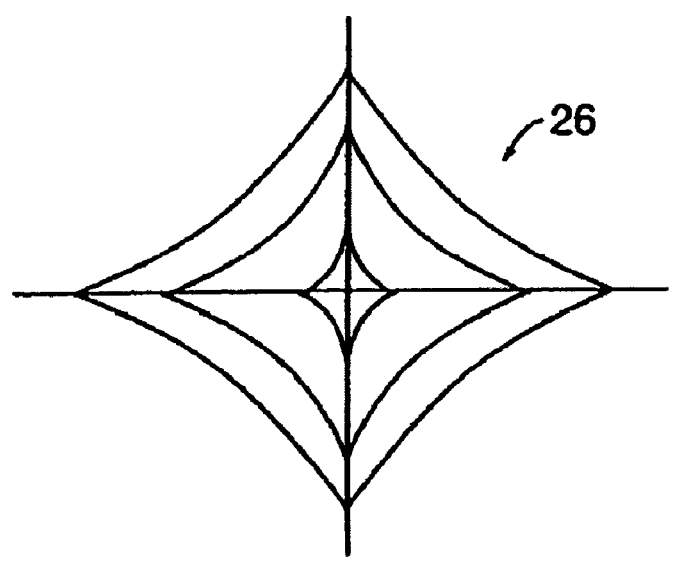
FIG. 4A illustrates a top view of a web-shaped profile embodiment of a one-piece construction of at least a distal end portion of a medical retrieval basket removed from a single piece of substantially flat material according to the invention.
Figure 4B:
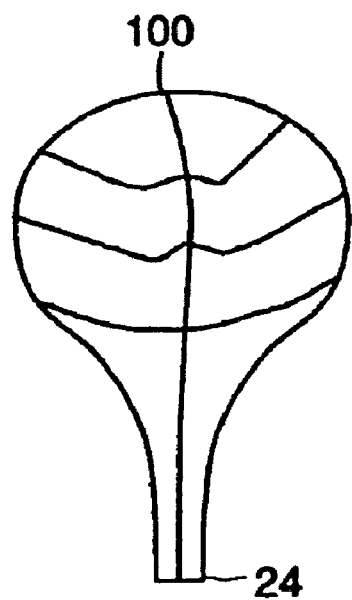
FIG. 4B illustrates a side view of an embodiment according to the invention of a three-dimensional atraumatic basket formed by bending and shaping the profile of the web-shaped profile illustrated in FIG. 4A.

In another embodiment, the basket can be made by extracting a single unit web-shaped profile 26, as illustrated in FIG. 4A, from a single piece of sheet-like material. The web-profile is removed from a single piece of sheet-like material by stamping, etching or cutting, for example. The web-profile is subsequently shaped and molded around a ball shape by heat treatment, cold-forming, or other shaping processes to achieve a basket 10 as illustrated in FIG. 4B. The distal end 100 of this basket 10 is atraumatic and substantially tipless. The proximal end 24 of basket 10 can be joined to a cable (not shown) and the basket can be moved within the lumen of a sheath relative to the sheath in a manner similar to the basket illustrated in FIGS. 3C and 3D.

Figure 5A:
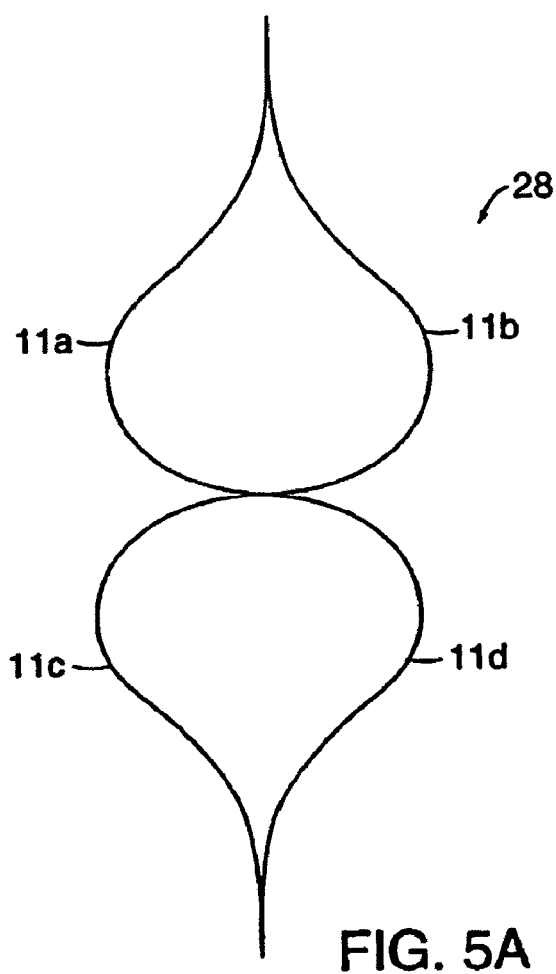
FIG. 5A illustrates a top view of a double loop-shaped profile embodiment of a one-piece construction of at least a distal end portion of a medical retrieval basket removed from a single piece of substantially flat material according to the invention.
Figure 5B:
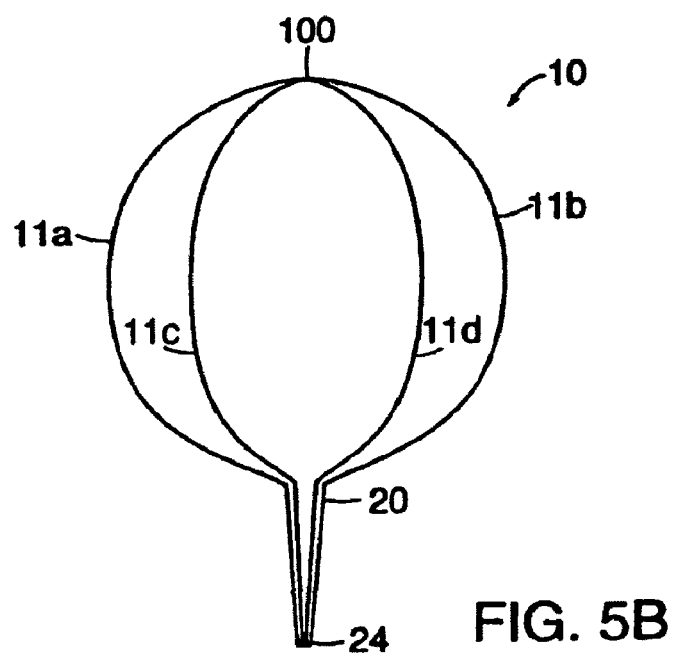
FIG. 5B illustrates a side view of an embodiment according to the invention of a three-dimensional atraumatic tipless basket formed by bending and shaping the profile of the double-loop shaped profile illustrated in FIG. 5A.

Referring to FIG. 5, another embodiment of the basket can be made by extracting a single unit double-loop profile 28 from a single piece of material by stamping, etching, or cutting, for example. The double-loop profile 28 is shaped and molded around a ball shape by heat treatment, cold-formed, or by other shaping processes, to form the basket 10 illustrated in FIG. 5B. The distal end 100 of the basket 10 is substantially tipless and atraumatic. The proximal end 24 of the basket can be joined to a cable (not shown) and the basket can be moved within the lumen of a sheath, relative to the sheath in a manner similar to the basket illustrated in FIGS. 3C and 3D.

To manufacture a basket according to the invention, a single piece of flat material, such as a sheet of metal, or a single piece of material contoured to conform to the basket radius is used to form the distal basket tip. When starting with a single piece of flat material, at least the distal basket tip is defined by a shape or profile that is removed from the single piece of construction material. The profile can be removed from the material by a variety of methods including, for example, stamping, etching, photoetching, or laser cutting as illustrated in FIG. 1A or 3A. The profile removed from the single piece of material is then shaped by heat treatment, cold-forming process or by other processes known in the art to form at least a distal end portion 5 as illustrated, for example, in FIGS. 1G and 6B having an atraumatic distal tip, or a three-dimensional basket structure, for example, as illustrated in FIGS. 1B, 3B, 4B and 5B having an atraumatic distal tip. Alternatively, the basket legs may be rotated or twisted slightly around their longitudinal axis to achieve a helical basket, for example, as shown in FIG. 1D.

A basket according to the invention also can be formed by injection molding the distal basket portion or desired basket profile. Alternatively, with a metal or plastic injection molding process, the three-dimensional distal basket portion or basket design can be injected into a three-dimensional mold thereby obviating the step of shaping the distal basket portion or basket structure following removal of the profile from a single piece of construction material by molding into a final shape.

The basket 10 and basket designs described below are joined at the basket proximal end to the distal end of the elongated member 18 to form a subassembly. The basket/elongated member subassembly is inserted into the sheath 12 and joined to the handle 8 to form the medical retrieval device according to the invention.

Figure 6B:
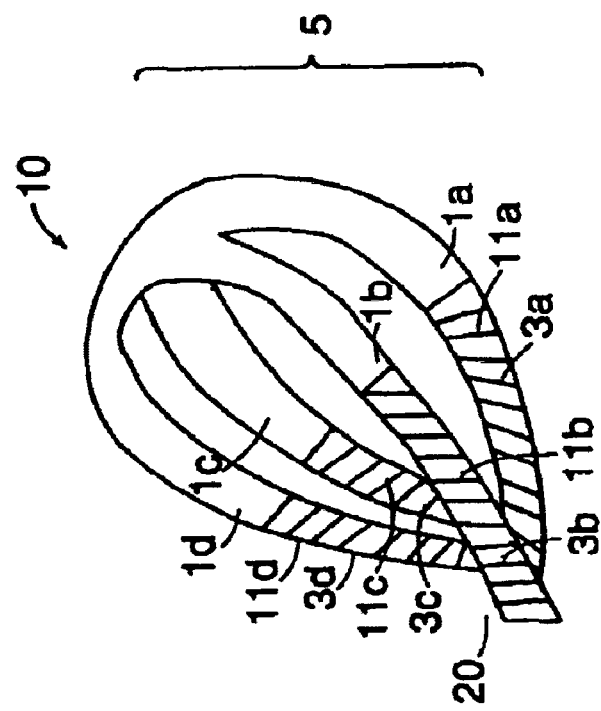
FIG. 6B is an embodiment according to the invention of a three-dimensional tipless basket with a distal end portion constructed from the profile illustrated in FIG. 6A.
Figure 6A:
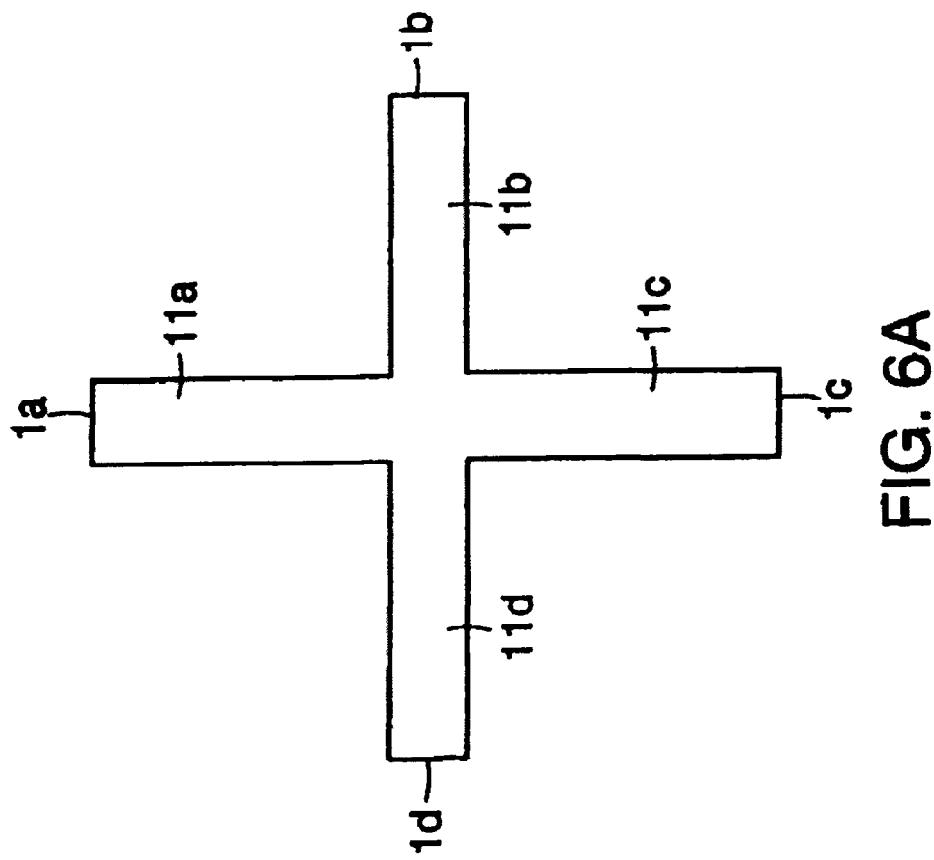
FIG. 6A is a top view of a stamped profile that can be formed into a basket or a portion of a basket by bending the legs of the shape, in accordance with the invention.

The "X" profile that is shown in FIG. 6A, for example, can be replaced by any other shape that lends itself to clinical efficiency and manufacturability and that results in a substantially tipless atraumatic basket. The "X" or other profiles can have a small, atraumatic protrusion or depression at the distal basket tip. Also, the "X" profile or other profile, can be shaped to make a distal end portion 5 of the basket 10, and leg extensions 3a, 3b, 3c, 3d can be added to end-sections 1a, 1b, 1c, 1d of legs 11a, 11b, 11c, 11d to form all of or a portion of the basket legs 11a, 11b, 11c, 11d as shown in FIG. 6B. Alternatively, the end-sections 1a, 1b, 1c, 1d of the basket legs 11a, 11b, 11c, 11d of the "X" profile or any other profile can be secured together at the base 20 of the basket 10 illustrated in FIG. 7A.

All or a portion of the inner surface (side toward basket center) of one or more of the basket legs can be treated to enhance the ability of the basket to grasp and hold material to be retrieved. For example, an anti-slip coating, such as a rubberized or plastic coating can be applied to at least a portion of the inner surface of at least one of the basket legs as illustrated on the inner surface 15 of leg 11b in FIG. 7A. The coating can be applied directly to the single piece of sheet-like material from which the basket profile is extracted before basket formation or to the inner surface of the basket legs after basket formation. An enhanced grasping and/or fragmentation capability also can be achieved by adding texture to at least the inner surface of at least one of the basket legs by, for example, creating serrations, teeth, or points on the inner surface(s). This can be achieved by, for example, etching, pitting, bending, stamping or machining the texture/roughness into the inner surface(s) by application of these methods directly to the single piece of sheet-like material from which the basket or basket distal end shape is extracted before basket formation, or directly to the inner surface of the basket legs after basket formation.

Referring to FIGS. 6A, 7B, and 8, according to one embodiment of the invention, a profile stamped from a single piece of sheet-like material has end-sections 1 that are brought together at a basket base 20 to form a three-dimensional basket 10. Alternatively, as illustrated in FIGS. 6A and 6B, just the distal end portion 5 of the basket can be formed from the single piece of construction material with the legs of the basket extending from the end-sections 1a, 1b, 1c, 1d of the profile and then drawing the end-sections 1a, 1b, 1c, 1d down and bringing the end-sections together at the basket base 20 to form the basket 10. As shown in FIG. 8, it is possible to have more than three or four basket legs by forming the basket distal end from, for example, an eight-leg 11a, 11b, 11c, 11d, 11e, 11f, 11g, 11h star-shape profile 28 extracted as a single unit from a single piece of sheet-like material. The shape forming the distal end portion of the basket may be asymmetrical.

Figure 10:
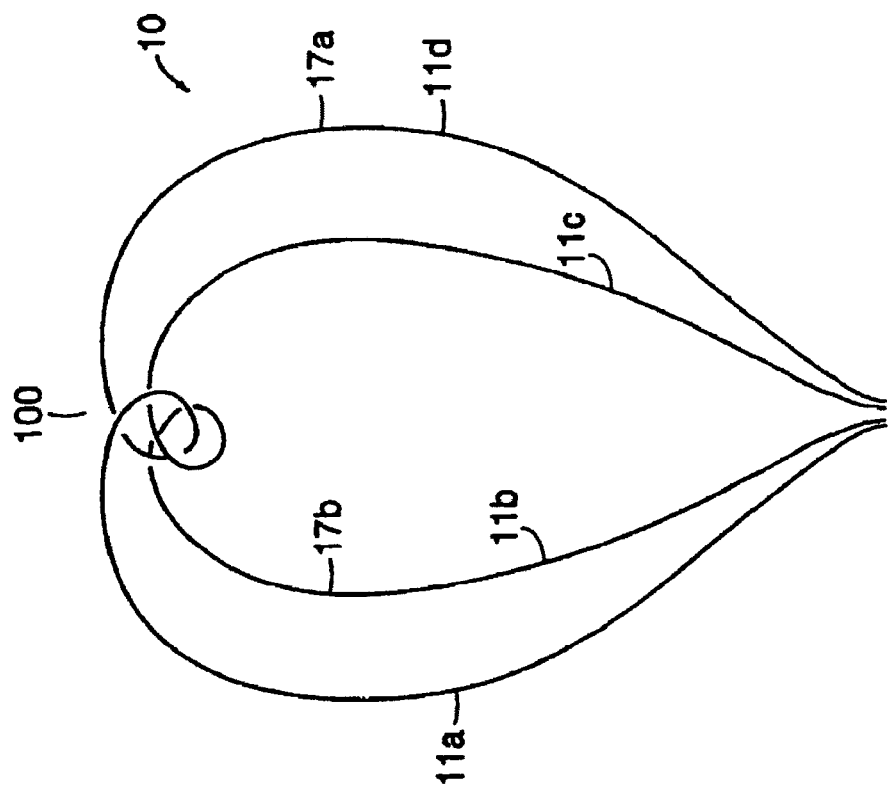
FIG. 10 illustrates an embodiment according to the invention of a basket with an atraumatic looped tip.
Figure 9:
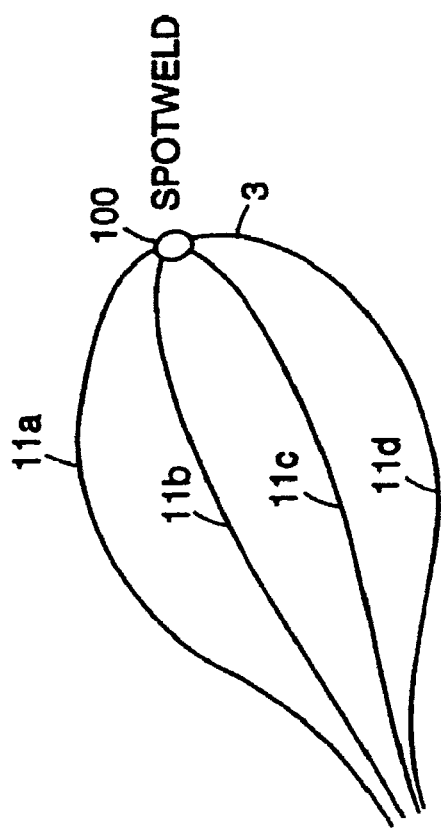
FIG. 9 illustrates an embodiment according to the invention of a basket with an atraumatic spot-welded tip.

Baskets that are atraumatic and tipless may also have each leg 11a, 11b, 11c, 11d joined at the distal end 100 of the basket in a variety of ways such as by spot welding the legs at the distal end 100 as illustrated in FIG. 9 or by looping two or more wires 17a, 17b together at the distal end 100 as illustrated in FIG. 10. The wires are looped together by forming a loop in a mid-portion of the first wire 17a. Second wire 17b is passed through the loop of the first wire 17a. The second wire 17b is looped within and is held by the loop of the first wire 17a.

Figure 11A:
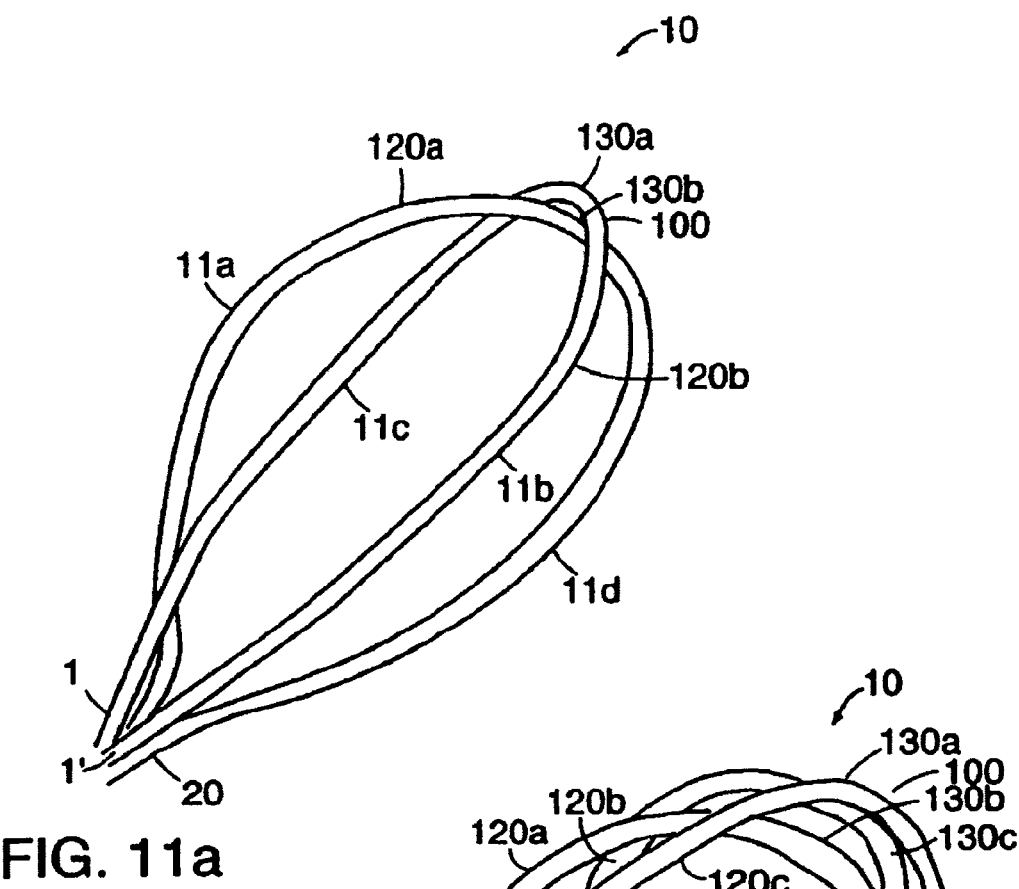
FIG. 11A illustrates a loop of a basket according to the invention.
Figure 11B:
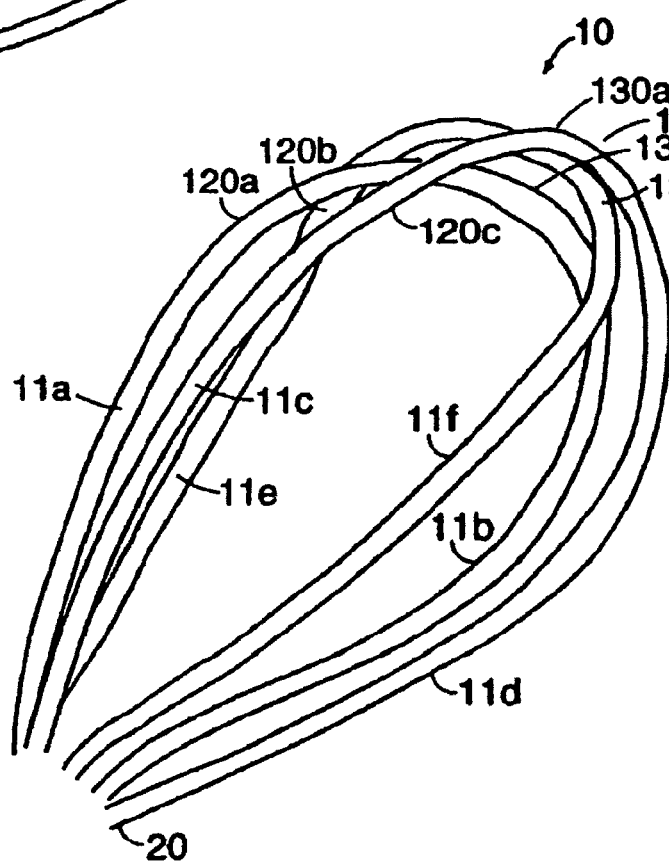
FIG. 11B illustrates an embodiment of a three-dimensional basket according to the invention formed from a plurality of basket loops illustrated in FIG. 11A.

Referring to FIGS. 11A and 11B, in another embodiment of the invention, a tipless end 130 of the atraumatic basket 10 is constructed by using single wires to form loops 120a, 120b having legs 11a, 11b, 11c, 11d extending from the apex 130a, 130b of the loops 120a and 120b, respectively, the apex 130a, 130b positioned at the basket distal end 100. A plurality of pre-formed wire loops is included in a three-dimensional, atraumatic basket. Wire loops may be formed from plastics, superelastic materials, stainless steel, shape memory metals, ceramic composites, other composites, or other materials and may have any of a variety of cross sectional shapes such as D-shape, B-shape, U-shape, round, half-round, oval, rectangular or ribbon-like. In this embodiment of an atraumatic wire basket, two wire loops 120a, 120b, for example, may be used to form a basket with four legs 11a, 11b, 11c, 11d as shown in FIG. 11A, and time wire loops 120a, 120b, 120c may be used to form a basket with six legs 11a, 11b, 11c, 11d, 11e, 11f as shown in FIG. 11B. Additional wire loops may be used to form a basket with more than the four or six legs shown. The apex 130 of each wire loop 120 intersects the apex 130 of the other wire loops 120 of the basket 10 at the basket distal end 100. The wire loops 120 at the basket distal end 100 are free to slide by one another, i.e., they are not affixed, fused, soldered, welded, glued, joined, secured or attached to one another. The advantages of this configuration of the basket is that the basket end 100 is atraumatic and provides flexibility thereby enhancing the ease by which stones are captured. The two end-sections 1, 1' of each wire loop are brought together at the basket base 20 and held in place by welding, soldering, ligating, gluing, crimping or any other means known in the art. In one embodiment, the end-sections 1, 1' of the wire loops are affixed (not shown) to a cable, coil, shaft, mandril wire or guidewire 18 that runs longitudinally in a sheath 12 as shown in FIG. 1E and FIG. 1F.

Figure 11D:
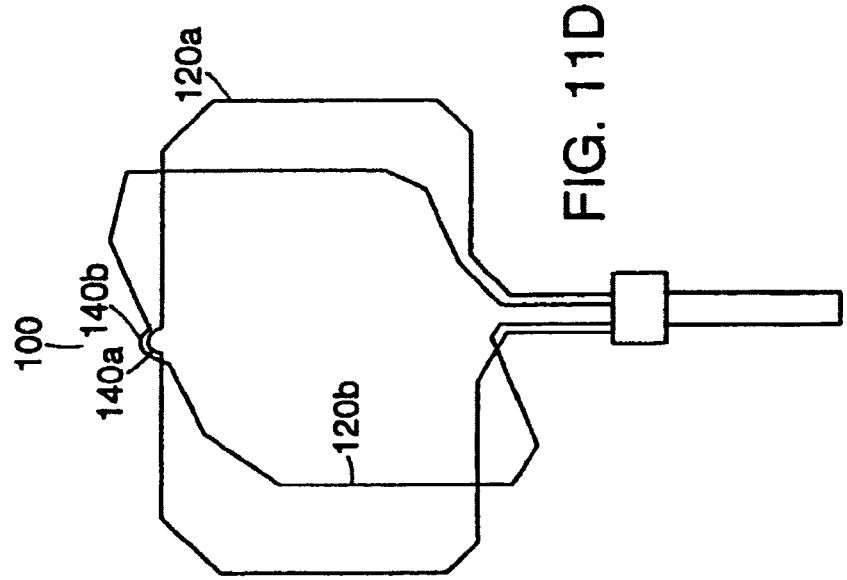
FIG. 11D illustrates an embodiment of a three-dimensional basket according to the invention formed from a plurality of basket loops illustrated in FIG. 11C.
Figure 11C:
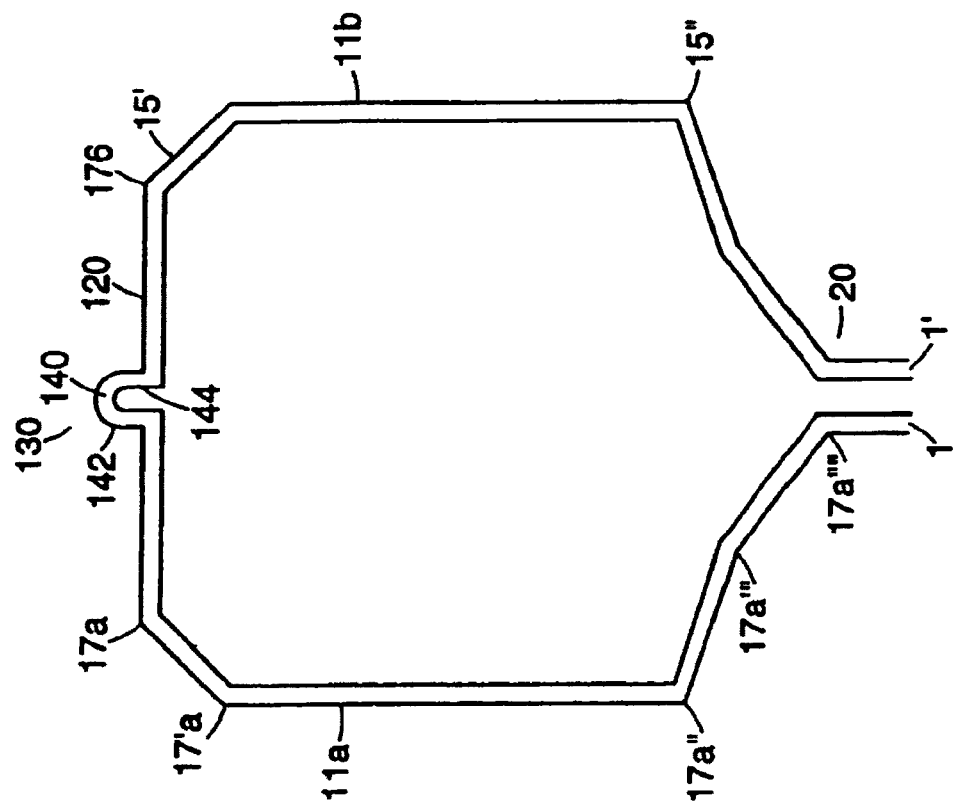
FIG. 11C illustrates a loop of a basket according to the invention having an atraumatic protrusion with a radius at the distal end.

Referring to FIGS. 11C and 11D, the tipless end 100 of the atraumatic basket can also be constructed by using single pre-formed wires to form modified loops 120, each modified loop having a pair of legs 11a, 11b extending from the apex 130 of the loop 120, the apex 130 positioned at the basket distal end 100. The apex 130 of a pre-formed wire loop 120 forming pairs of basket legs is modified to stabilize the basket tip. For example, as illustrated in FIG. 11C, the apex 130 of a wire loop 120 is modified by a protrusion 140 with a radius, such as a semi-circular protrusion. A basket may be formed by a plurality of wire loops 120a, 120b, each wire loop having a small protrusion 140a, 140b with a radius, as illustrated in FIG. 11D. Each semi-circular protrusion on the basket wire has a convex surface 142 and a concave surface 144 as illustrated in FIG. 11C. In this embodiment, the convex surface 142 of the semi-circular protrusion 140 of wire loop 120a meets the concave surface 144 of the semi-circular protrusion 140 of the outer wire loop 120b where the wires of the basket cross one another at the basket distal tip 100 as illustrated in FIG. 11D. At the apex 130 where the loops cross one another at the distal end of the basket, the wires forming the loops are not adhered, affixed, fused, soldered, welded, glued or joined to one another. Typically, two or more wires (i.e., loops), each with a semi-circular protrusion, are used to form an atraumatic wire basket.

Wire loops 120 may be formed from superelastic materials, stainless steel, shape memory metals, ceramic composites, other composites, or other materials and may have any of a variety of cross sectional shapes such as D-shape, B-shape, U-shape, round, half-round, oval, rectangular, or ribbon-like. In this embodiment of an atraumatic wire basket, for example, two wire loops 120a, 120b may be used to form a basket with four legs as shown in FIG. 11C, or three wire loops may be used to form a basket with six legs (not shown), and so on. Additional wire loops may be used to form a basket with more than the four or six legs shown. Referring to FIG. 11C, the two end-sections 1, 1' of each wire loop are brought together at the basket base 20 and held in place by welding, soldering, ligating, gluing, crimping or any other means known in the art. The end-sections 1, 1' of the wire loops can be affixed as shown in FIG. 11D to a cable, coil, shaft, mandril wire or guidewire 18 that runs longitudinally in a sheath 12 as shown in FIG. 1E and FIG. 1F. A channel 200 may run through the sheath 12 and the proximal end 20 of the basket 10 to accommodate a ram-rod, laser or other lithotriptic device 9 as shown in FIG. 1H and described earlier.

A basket of the invention having two or more wire loops 120a, 120b each with semi-circular protrusions 140 at the apex 130 of the loops 120a, 120b, has enhanced basket stability and dilatative strength without substantially compromising basket flexibility. In this embodiment of the invention (FIGS. 11C and 11D), the wires are unlikely to slide by one another at the distal tip. The semi-circular protrusions also help to reduce the stress on the basket legs while closing the basket.

Figure 12A:
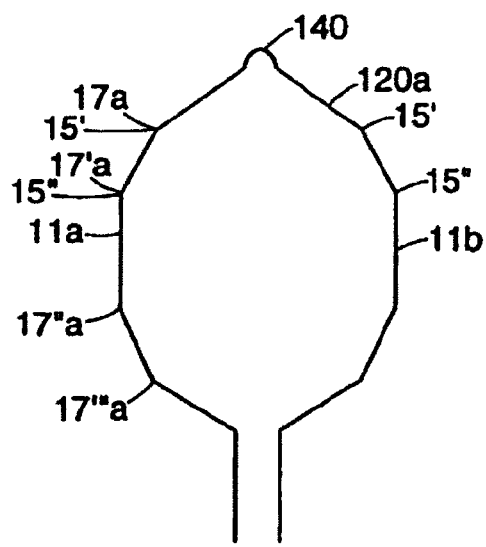
FIG. 12A illustrates another embodiment of the basket loop having multiple shoulders illustrated in FIG. 11C.
Figure 12B:
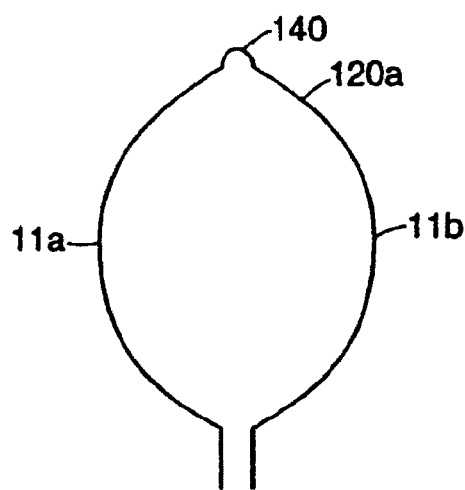
FIG. 12B illustrates yet another embodiment of the basket loop illustrated in FIG. 12A.
Figure 12C:
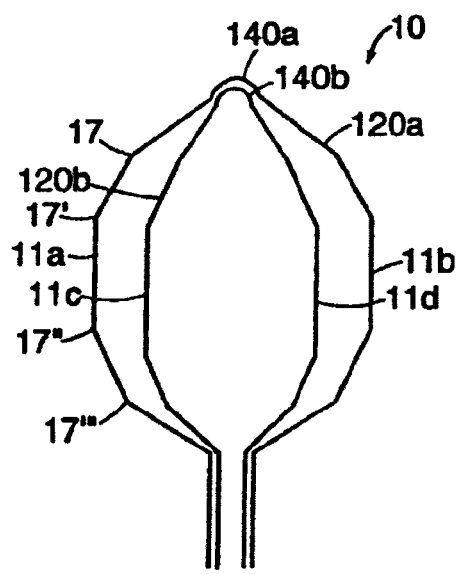
FIG. 12C illustrates an embodiment of a three-dimensional basket formed from basket loops having multiple shoulders illustrated in 12A.
Figure 12D:
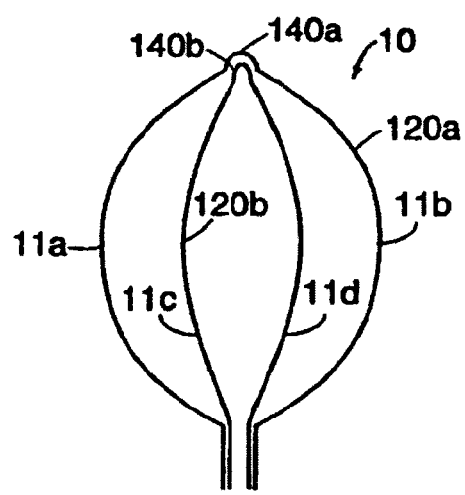
FIG. 12D illustrates an embodiment of a three-dimensional basket formed from basket loops illustrated in FIG. 12B.

The legs of an atraumatic wire basket 10 illustrated in FIGS. 11A-11D and FIGS. 12A-12D may be gently curved or may have a plurality of angular bends. In one embodiment, illustrated in FIG. 12A, each of the legs 11a, 11b of a loop 120a have five angular bends, 17a, 17a', 17a", 17a''', 17a'''' forming at least two shoulders 15' and 15" on each leg 11a, 11b of the wire loop 120. A three-dimensional basket shape formed by two loops 120a, 120b of the type illustrated in FIG. 12A is shown in FIG. 12B. FIG. 12A illustrates a wire loop 120 configuration where all of the angles 17 of the loop are obtuse. A three-dimensional basket shape formed by two loops 120a, 120b of the type illustrated in FIG. 12A is shown in FIG. 12C. An infinite number of obtuse angles in both legs of the wire loop results in a smoothly curved loop as illustrated in FIG. 12B. A largely oval or round, atraumatic three-dimensional basket shape 10 formed by two basket loops 120a, 120b of the type illustrated in FIG. 12B is shown in FIG. 12D. The legs 11a, 11b, 11c, 11d of the baskets illustrated in FIGS. 11B, 11D, 12C and 12D may be pre-formed, and their cross-section may be B-shaped, D-shaped, U-shaped, round, half-round, oval, rectangular, ribbon-like, or a variety of other cross-sectional shapes such as those shown in FIGS. 2D and 2E.

Figure 13C:
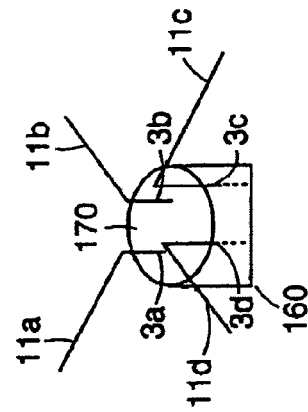
FIG. 13C illustrates the details of the inverted cap illustrated in FIGS. 13A and 13B.
Figure 13A:
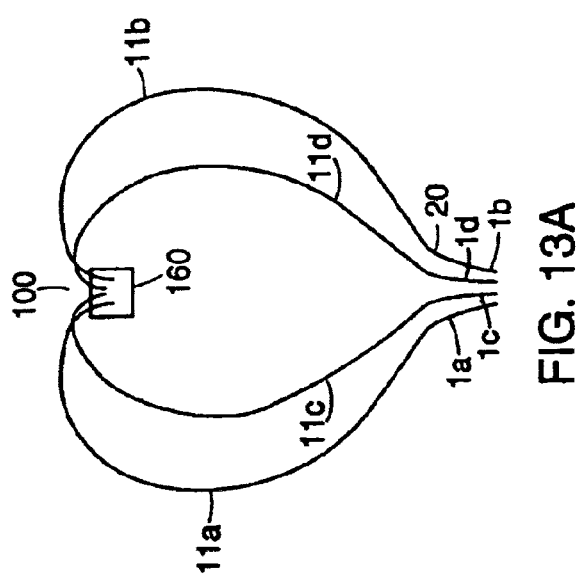
FIG. 13A illustrates an inverted cap embodiment of a tipless basket.
Figure 13B:
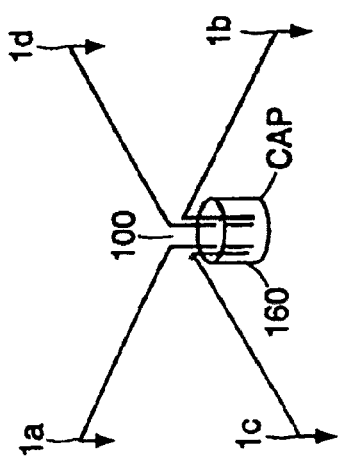
FIG. 13B illustrates the distal end portion of the inverted cap, tipless basket illustrated in FIG. 13A before the ends of the basket legs are affixed together at the proximal end of the basket.

In yet another embodiment of an atraumatic wire basket illustrated in FIG. 13A, the distal ends 3a, 3b, 3c, 3d of the basket wires 3 insert into a cap 160 with a core 170 at the basket tip 100 as shown in FIG. 13C. The distal ends 3a, 3b, 3c, 3d of the wires are affixed to the cap 160 by soldering, gluing or any means known in the art. The wires emerging from the cap are bent and then drawn down proximally as indicated by the arrows in FIG. 13B to form basket legs 11a, 11b, 11c, 11d. The end-sections of the legs 1a, 1b, 1c, 1d are gathered together at the basket base 20 to form an atraumatic wire basket 10 as shown in FIG. 13A. The end-sections 1a, 1b, 1c, 1d can be joined to a cable, shaft or coil (not shown).

Figure 14:
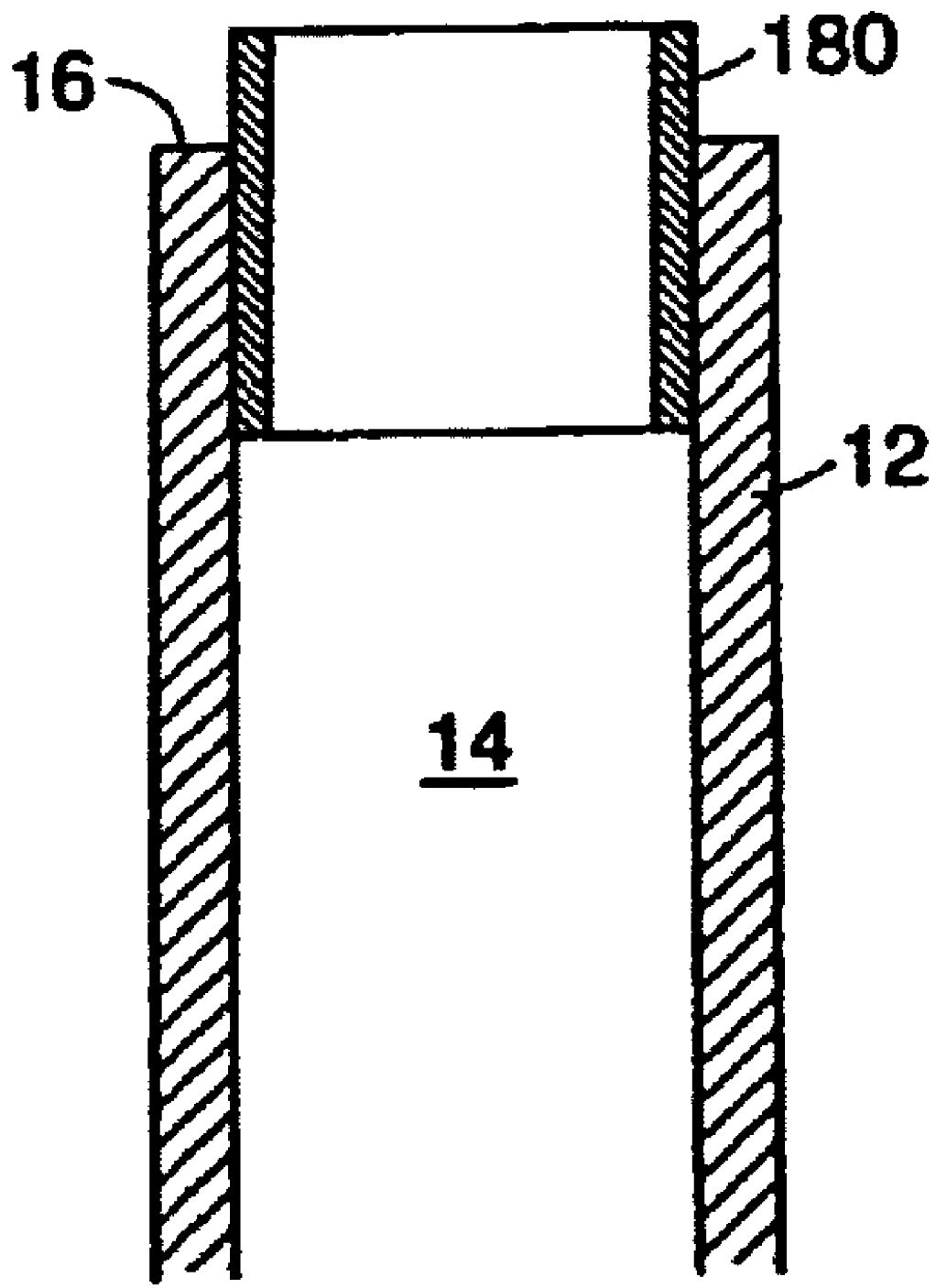
FIG. 14 illustrates a metal ring inserted into a polyimide sheath before the metal ring is ground flush with the end of the polyimide sheath.

In some embodiments of the invention, the sheath 12 of the medical retrieval device is manufactured from polyimide, PTFE, composites or similar materials. In order to prevent the distal end 16 of a polyimide sheath 12 from splitting, a metal ring 180, as illustrated in FIG. 14, is inserted into the lumen 14 of the distal end 16 of a polyimide sheath 12. The metal ring 180 is flush with the end 16 of the polyimide sheath or may protrude slightly beyond the end of the sheath as illustrated in FIG. 14.

In yet another aspect, the invention relates to a method for retrieving material from a body such as a body tract or body canal. Material (e.g., biological or foreign) can be retrieved from a body by using a tipless basket where at least a distal portion of the basket is defined by a shape which comprises a single unit or by using an atraumatic wire loop basket, each basket wire forming a loop with a distal atraumatic protrusion. The basket of the retrieval device has a tipless or an atraumatic distal end and thus allows the capture of material that is located in pockets or other difficult-to-access areas within the body. Because the distal basket end is atraumatic, it can make intimate contact with the surface of tissue, even the walls or lining of a pocket-type area, and allows the retrieval of stones or other materials that are unrecoverable with conventional tipped baskets that can cause tissue trauma and are limited, by the existence of the protruding tip, in how close the basket can approach the tissue. A method for retrieving material from a body includes inserting a retrieval device with an atraumatic basket into the body, moving the tipless basket into the extended position, maneuvering the basket via one or more actuators on the proximal handle (which is located outside of the body) of the retrieval device until the material (e.g., stone) is entrapped within the three-dimensional basket structure, and capturing the material within the basket by moving the basket relative to the sheath to close the basket legs around the material. With the material so gripped or held by the basket, the basket can be withdrawn from the body to remove the material from the body. Before the basket is withdrawn from the body with the captured material, the material can be broken apart by, for example, laser energy or lithotripsy. Mechanisms for breaking up the material before its removal from the body can be part of the retrieval device or can be separate tools/devices that are also inserted into the body and utilized at the appropriate time in the stone removal procedure. The material that can be captured with tipless baskets according to the invention includes a thrombus, embolus, foreign body, calculus, or a stone, such as a kidney stone, a ureteral stone, a urinary bladder stone, a gall bladder stone, a stone within the biliary tree, tumor, polyp or foreign body.

Variations, modifications, and other implementations of what is described herein will occur to those of ordinary skill in the art without departing from the spirit and the scope of the invention as claimed. Accordingly, the invention is to be defined not by the preceding illustrative description but instead by the spirit and scope of the following claims.

What is claimed is:

1. A medical retrieval device, comprising:
    a sheath;
    a handle at a proximal end of the sheath; and
    a basket of a single piece of material, the basket for removing material from a body and including:
        an elongated member at a proximal end of the basket including a first portion and a second portion distinct from the first portion; and
        a plurality of legs, each leg including a proximal end and a distal end, wherein the distal end of each of the plurality of legs is joined to the distal end of each of the other plurality of legs at a distal end of the basket, the proximal ends of a first set of the plurality of legs are joined at the first portion of the elongated member, and the proximal ends of a second set of the plurality of legs are joined at the second portion of the elongated member.

2. The medical retrieval device of claim 1, wherein the first portion and the second portion of the elongated member are substantially parallel.

3. The medical retrieval device of claim 1, wherein the first portion and the second portion of the elongated member are joined to a cable.

4. The medical retrieval device of claim 1, wherein the distal end of the basket includes an atraumatic tip.

5. The medical retrieval device of claim 1, wherein each of the plurality of legs includes a width, the width of each leg being tapered at the proximal end and the distal end of the leg.

6. The medical retrieval device of claim 1, wherein the first portion is a first single elongate member, and the second portion is a second single elongate member, and wherein the proximal ends of the first set of the plurality of legs are joined at the first single elongate member, and the proximal ends of the second set of the plurality of legs are joined at the second single elongate member.

7. A medical retrieval device, comprising:
    a sheath having a proximal end and a distal end;
    a handle at the proximal end of the sheath; and
    a basket for removing material from a body, the basket formed by removing a flat one-piece basket profile from a single sheet of material and shaping the one-piece basket profile, wherein the one-piece basket profile is one of hourglass-shaped and double-looped, the basket having a collapsed position where the basket is enclosed within the sheath and an expanded position where the basket is beyond the distal end of the sheath, the basket further comprising a plurality of legs joined at a distal end of the basket.

8. The medical retrieval device of claim 7, wherein the one-piece basket profile is hourglass-shaped.

9. The medical retrieval device of claim 7, wherein the distal end has a substantially atraumatic tip.

10. The medical retrieval device of claim 7, wherein removing the one-piece basket profile comprises one of stamping, etching, photoetching, and laser cutting.

11. The medical retrieval device of claim 7, wherein shaping the one-piece basket profile includes folding the one-piece basket profile.

12. The medical retrieval device of claim 7, further comprising an elongated member at a proximal end of the basket, the elongated member including a first single elongate member and a second single elongate member distinct from the first single elongate member, wherein a first set of the plurality of legs is joined at the first single elongate member, and a second set of the plurality of legs is joined at the second single elongate member.

13. A structure for making a medical retrieval device, comprising:

an hour-glass shaped material having a first set of legs and a second set of legs, the proximal ends of the first set of legs being joined together at a proximal end of the material, the distal ends of the first set of legs being joined together between the proximal end and a distal end of the material, the distal ends of the second set of legs being joined together at the distal end of the material, and the proximal ends of the second set of legs being joined together between the proximal end and the distal end of the material.

14. The structure of claim 13, wherein the material is substantially flat.

15. The structure of claim 13, wherein the distal ends of the first set of legs are joined to the proximal ends of the second set of legs.

16. The structure of claim 13, wherein an elongate member extends from the distal ends of the second set of legs.

17. The structure of claim 16, wherein an elongate member extends from the proximal ends of the first set of legs.

18. The structure of claim 13, wherein the material is one-piece.

19. The structure of claim 13, wherein all of the proximal ends of the first set of legs converge to a first single connection point, and all of the distal ends of the second set of legs converge to a second single connection point.

* * * * *